United States Patent [19]

Pews

[11] Patent Number: 4,996,323

[45] Date of Patent: Feb. 26, 1991

[54] PROCESS FOR THE PREPARATION OF 3,5,6-TRICHLOROPYRIDIN-2-OL

[75] Inventor: R. Garth Pews, Midland, Mich.

[73] Assignee: The Dow Chemical Company, Midland, Mich.

[21] Appl. No.: 350,961

[22] Filed: May 12, 1989

[51] Int. Cl.$^5$ .............................................. C07D 213/64
[52] U.S. Cl. .................................. 546/250; 546/303; 558/398; 558/440; 558/441
[58] Field of Search ................ 546/303, 250; 558/398, 558/440, 441

[56] References Cited

U.S. PATENT DOCUMENTS

| | | | |
|---|---|---|---|
| 3,007,931 | 11/1961 | Simpson et al. | 558/440 |
| 4,245,098 | 1/1981 | Steiner et al. | 546/250 |
| 4,327,216 | 4/1982 | Martin | 546/250 |
| 4,435,573 | 3/1984 | Lysenko et al. | 546/250 |
| 4,465,186 | 8/1984 | Steiner et al. | 558/440 |
| 4,468,354 | 8/1984 | Lysenko et al. | 546/250 |
| 4,469,896 | 9/1984 | Steiner et al. | 568/495 |

FOREIGN PATENT DOCUMENTS 63-313771  12/1988  Japan ................... 546/303

*Primary Examiner*—Mary C. Lee
*Assistant Examiner*—Jacqueline Haley
*Attorney, Agent, or Firm*—Craig E. Mixan; Ronald G. Brookens

[57] ABSTRACT

The preparation of 3,5,6-trichloropyridin-2-ol from trichloroacetyl chloride and acrylonitrile is improved by separately conducting the individual addition, cyclization and aromatization steps. By separating the steps, water and HCl, by-products of the latter steps, can be precluded from interfering with the earlier steps. The individual process steps have also been improved.

10 Claims, No Drawings

PROCESS FOR THE PREPARATION OF 3,5,6-TRICHLOROPYRIDIN-2-OL

FIELD OF THE INVENTION

The present invention is directed to an improved process for preparing 3,5,6-trichloropyridin-2-ol from trichloroacetyl chloride and acrylonitrile.

BACKGROUND OF THE INVENTION 3,5,6-Trichloropyridin-2-ol is an intermediate in the manufacture of several agricultural pesticides, e.g., chlorpyrifos, chlorpyrifos-methyl and triclopyr. U.S. Pat. No. 4,327,216 describes a process for preparing a mixture of 2,3,5,6-tetrachloropyridine and 3,5,6-trichloropyridin-2-ol by reacting trichloroacetyl chloride with acrylonitrile in the presence of a catalyst.

The following series of reactions is responsible for the products obtained in said patent (Scheme I).

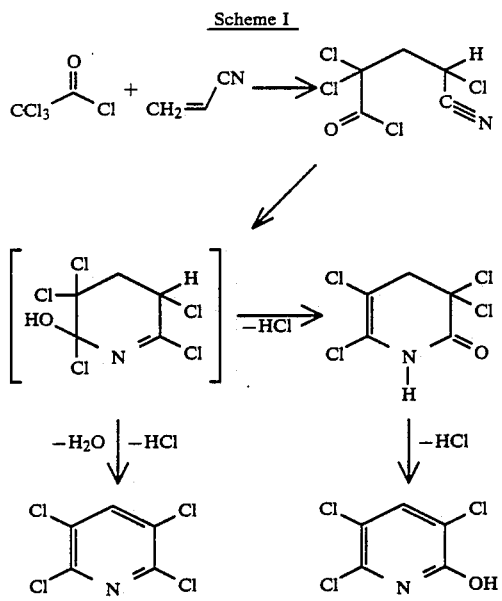

Scheme I

Although the series of reactions is advantageously carried out in a single operation and in a closed system under pressure, the combined yield of 2,3,5,6-tetrachloropyridine and 3,5,6-trichloropyridin-2-ol is not very high. Furthermore, the reaction typically produces a mixture of the two products which must be separated or treated in subsequent operations to convert one product into the other. It is desirable to have a process to prepare 3,5,6-trichloropyridin-2-ol in higher yields and without any tetrachloropyridine by-product.

SUMMARY OF THE INVENTION

The present invention is directed to an improved process for preparing 3,5,6-trichloropyridin-2-ol which comprises the following steps:
(a) contacting trichloroacetyl chloride with acrylonitrile in the presence of a catalytic amount of a cuprous salt to produce 2,2,4-trichloro-4-cyanobutanoyl chloride under conditions which allow for the removal of HCl;
(b) contacting the 2,2,4-trichlor-4-cyano-butanoyl chloride in an inert organic solvent with an anhydrous acid under pressure at a temperature below 100° C. to cyclize the butanoyl chloride to 3,3,5,6-tetrachloro-3,4-dihydropyridin-2-one; and
(c) converting the 3,3,5,6-tetrachloro-3,4-dihydropyridin-2-one to 3,5,6-trichloro-pyridin-2-ol.

The present invention is further directed to the various process improvements as they relate to the individual steps.

DETAILED DESCRIPTION OF THE INVENTION

It has been found that 3,5,6-trichloropyridin-2-ol can be prepared in high yield and without tetrachloropyridine as a by-product by conducting the addition, cyclization and aromatization reactions separately.

Addition

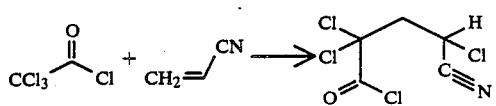

Cyclization

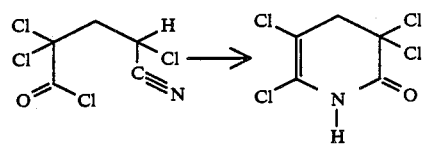

Aromatization

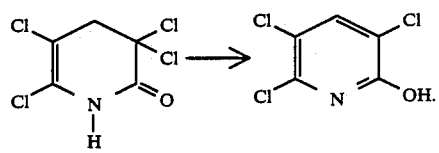

The first reaction, the addition reaction of trichloroacetyl chloride to acrylonitrile produces 2,2,4-trichloro-4-cyanobutanoyl chloride, which cyclizes in the presence of HCl. The cyclization intermediate, depending on whether HCl or $H_2O$ is eliminated, can yield one of three products: 3,3,5,6-tetrachloro-3,4-dihydropyridin-2-one; 3,5,6-trichloropyridin-2-ol; or 2,3,5,6-tetrachloropyridine.

It has now been found that the water produced during the formation of the tetrachloropyridine is a major contributor to yield loss via numerous side reactions. Since water can be formed during the cyclization process and since the cyclization is acid catalyzed, better yields are achieved by removing any HCl formed by decomposition of the reactants during the addition step. For convenience, HCl is removed and hence water formation is precluded by preferentially conducting the addition reaction under reflux.

Trichloroacetyl chloride (TCAC) and acrylonitrile (VCN) are items of commerce and are routinely distilled prior to use. The trichloroacetyl chloride and acrylonitrile can be contacted in molar ratios ranging from stoichiometric, i.e., 1:1, to a 2 to 3 fold excess of either reagent, i.e., 1:3 to 3:1 VCN/TCAC. Ratios of VCN/TCAC of 1.1 to 1.3 are generally preferred.

The addition reaction is carried out in the presence of a catalytic amount of a cuprous salt under an inert atmosphere, such as, for example, nitrogen or argon. Cuprous salts that can be employed include, for example, the chloride, bromide, iodide, oxide or acetate, preferably the halides. Catalysts that are partially oxidized to the cupric oxidation state or are hydrated are less effective than the pure materials. The addition of copper metal, which itself can be oxidized to the cuprous oxidation state while simultaneously preventing further oxidation to the cupric oxidation state, can advantageously be employed. The cuprous catalyst is usually employed in an amount corresponding to from about 0.005 to about 0.05 moles of catalyst per mole of trichloroacetyl chloride, although larger proportions can be used.

The cuprous catalyzed addition of polyhalogen compounds to olefins is often conducted in the presence of a cocatalyst, such as an alcohol, amine or phosphine, which helps solubilize the cuprous salt. Since alcohols and amines react with acid chlorides, they cannot be used in the present invention. Unlike the addition of other polyhalogen compounds to olefins, rather than enhancing the rate of the present reaction, phosphines actually inhibit it.

The addition reaction may be carried out neat or in the presence of an inert solvent. Alkylnitriles, such as acetonitrile, are commonly used for the cuprous catalyzed addition of polyhalogen compounds to olefins. However, the addition of acetonitrile to the reaction mixture does not provide any beneficial effects. Therefore, the reaction is preferably conducted neat or with excess TCAC or VCN effectively serving as the solvent. Trichloroacetyl chloride can be commercially prepared by the photochemical oxidation of perchloroethylene: see, for example, U.S. Pat. No. 2,427,624. Prepared by this procedure, TCAC typically contains about 15 percent residual perchloroethylene. Perchloroethylene has no negative effect on the addition chemistry.

To prevent the production of HCl by the premature cyclization of 2,2,4-trichloro-4-cyanobutanoyl chloride, reaction temperatures should be maintained below 140° C. To remove any HCl produced by the decomposition of TCAC, the reaction is run at reflux. The reflux temperature is determined by the composition of the mixture. Ideally, the temperature should be maintained between 70°–120° C., preferably between 80°–105° C. The preferred temperatures are conveniently between the boiling points of VCN and TCAC at atmospheric pressure. When the reaction is conducted neat or with VCN or TCAC in excess as an effective solvent, the reflux temperature gradually increases as the lower boiling reactants are converted to higher boiling product.

The addition reaction is preferably conducted under an inert atmosphere, such as, for example, under a nitrogen or argon blanket. Although conveniently conducted at atmospheric pressure, the reaction is preferably run under a slight positive pressure of up to about 5 pounds per square inch (psig) of the blanketing inert gas which helps in keeping the reaction mixture dry.

In a typical reaction, freshly distilled TCAC, VCN and anhydrous CuCl are heated under reflux in a nitrogen atmosphere. After the addition reaction is complete, generally in from about 8 to about 48 hours (hrs), the product 2,2,4-trichloro-4-cyanobutanoyl chloride can be recovered by conventional techniques. The product can be conveniently isolated, for example, by evaporating any volatile TCAC or VCN, adding a suitable solvent in which the spent copper catalyst is not soluble and in which the subsequent cyclization reaction can be advantageously conducted, and removing the catalyst by filtration. Suitable solvents include aromatic hydrocarbons, halogenated hydrocarbons and carboxylic acid esters. Product of greater than 90 percent purity can be obtained by evaporation of the solvent. Alternatively, the filtrate so obtained can be used directly in the subsequent cyclization reaction.

The cyclization of 2,2,4-trichloro-4-cyanobutanoyl chloride to 3,3,5,6-tetrachloro-3,4-dihydropyridin-2-one is catalyzed by acidic reagents, preferably in an anhydrous state. The cyclization is conveniently carried out, for example, by contacting the 2,2,4-trichloro-4-cyanobutanoyl chloride with anhydrous HCl. Simply sparging anhydrous HCl into the 2,2,4--trichloro-4-cyanobutanoyl chloride at atmospheric pressure in the absence of a solvent does not accomplish cyclization. Since higher temperatures lead to greater amounts of dehydration and tetrachloropyridine formation, it is beneficial to keep the temperature below 100° C. In order to keep the reaction mixture mobile at temperatures below the melting point of the product and in order to keep the anhydrous HCl in effective contact with the reaction mixture, it is preferable to conduct the cyclization under pressure in the presence of a solvent.

The cyclization reaction is effectively run from ambient temperature to about 100° C., preferably from about 40° to about 60° C. Pressures from about 5 to about 200 pounds per square inch (psig) are routinely employed: those from about 25 to about 150 psig are preferred.

Suitable solvents for the cyclization reaction include aromatic hydrocarbons, halogenated hydrocarbons and carboxylic acid esters. Examples of suitable solvents of each class include but are not limited to the following: toluene and xylenes; methylene chloride, ethylene dichloride (EDC) and perchloroethylene (PERC): and ethyl acetate.

The cyclization reaction may be conveniently conducted in a batch reaction or in a continuous fashion in a coil reactor. In a typical reaction, 2,2,4 ..ichloro-4-cyanobutanoyl chloride is diluted with the desired solvent in a closed pressure vessel, and the vessel is pressurized with anhydrous HCl to the desired pressure. The reaction mixture is stirred at the appropriate temperature until the reaction is completed, usually from about one to about three hours. The reaction vessel is vented and the product, 3,3,5,6-tetrachloro-3,4-dihydropyridin-2-one, can be isolated by conventional procedures. For example, evaporation of the solvent provides a crude solid product which can be slurried with an aliphatic hydrocarbon, such as hexane, and which can then be isolated by filtration. Product so obtained is sufficiently pure after drying to be used in the subsequent aromatization. Alternatively, the crude reaction mixture can be used directly, immediately after venting and removal of the HCl.

The aromatization of 3,3,5,6-tetrachloro-3,4-dihydropyridin-2-one to 3,5,6-trichloropyridin-2-ol can be accomplished in a variety of ways. Among the most effective procedures are treatment in a two-phase system with an aqueous base or treatment with chloride ion in an organic solvent.

Since the desired product, 3,5,6-trichloropyridin-2-ol, is often used as the sodium salt, it is often convenient to conduct the aromatization with aqueous alkaline solutions. The reaction is preferably run in a two-phase system using a water immiscible organic solvent. Suitable solvents for the aromatization reaction include aromatic hydrocarbons, halogenated hydrocarbons and carboxylic acid esters. Examples of suitable solvents of each class include but are not limited to the following: toluene and xylenes: methylene chloride, ethylene dichloride and perchloroethylene: and ethyl acetate. Naturally, it is preferable to employ the same solvent that has previously been used in the cyclization reaction.

The aromatization reaction requires the use of at least two equivalents of base per equivalent of 3,3,5,6-tetrachloro-3,4-dihydropyridin-2-one. One equivalent is required for the elimination of one mole of HCl, while the second equivalent is consumed in converting the pyridinol to the pyridinate. If desired, larger proportions of base may be employed. Suitable bases include but are not limited to the alkali metal hydroxides and carbonates. Sodium or potassium carbonate are generally preferred, particularly for the carboxylic acid ester solvents which are susceptible to reaction with dilute caustic at room temperature.

In a typical reaction, the base, dihydropyridone solvent and water are contacted with stirring at a temperature of from ambient to about 100° C. or the reflux temperature of the mixture. After the reaction is complete, generally in from about 2 to about 24 hrs, the 3,5,6-trichloropyridin-2-ol is isolated by conventional procedures. For example, trichloropyridinol may simply be isolated by acidifying the reaction mixture and separating the organic phase. After drying the organic solution, evaporation of the solvent provides the desired pyridinol. Alternatively, if the alkali metal salt of the trichloropyridinol is desired, an aqueous solution of the pyridinate may be obtained by simply separating the aqueous reaction phase.

Alternatively, the aromatization reaction can be accomplished by treating the 3,3,5,6-tetrachloro-3,4-dihydropyridin-2-one with chloride ion in an inert organic solvent. The chloride ion may be added directly or may be generated in situ by initiating the elimination of HCl from the pyridone. Since chloride ion is generated by the elimination of HCl from the substrate, only catalytic quantities of chloride ion or of a material capable of initiating the elimination of HCl are needed. Suitable catalysts contemplated by the above definition include but are not limited to the following types of materials: tertiary or aromatic amine bases, such as, for example, trialkyl amines, pyridine, picolines or lutidines: quaternary ammonium or phosphonium salts, such as, for example, tetraalkyl or aryl ammonium or phosphonium halides: crown ether complexes, such as, for example, 18-Crown-6/KCl; and ion exchange resins, particularly amine resins such as, for example, MSA-1 Dow Ion Exchange Resin. Specific examples of suitable materials include the following: tetrabutylammonium halides, tetraphenylphosphonium halides, nonyltriphenylphosphonium halides, benzyltriethylammonium halides, pyridinium halides and poly (4-vinylpyridine). MSA-1 Dow Ion Exchange Resin and tetrabutylammonium chloride are among the preferred catalysts. These catalysts are usually employed in an amount corresponding to from about 0.002 to about 0.2 moles of catalyst per mole of 3,3,5,6-tetrachloro-3,4-dihydropyridin-2-one, preferably from about 0.005 to about 0.05 moles of catalyst per mole of dihydropyridone.

Suitable solvents for the aromatization reaction include the same aromatic hydrocarbons, halogenated hydrocarbons and carboxylic acid esters employed in the previous steps. Perchloroethylene is a particularly preferred solvent for this reaction.

The reaction is conducted at a temperature from between about 40° to about 120° C., preferably at the reflux temperature of the mixture.

In a typical reaction, the 3,3,5,6-tetrachloro-3,4-dihydropyridin-2-one is contacted with the catalyst and solvent, and the reaction mixture is heated to reflux. After the reaction is complete, generally in from about 1 to about 3 hrs, the desired 3,5,6-trichloropyridin-2-ol can be isolated by conventional techniques. For example, if an insoluble catalyst such as MSA-1 Dow Ion Exchange Resin is employed, the catalyst can be removed by filtration while hot and can be recovered and recycled in subsequent reactions. After the removal of the catalyst, the reaction solution can be cooled to crystallize the trichloropyridinol which is then isolated by filtration. If a soluble catalyst such as tetrabutylammonium chloride is used, the reaction solution can be cooled to crystallize the trichloropyridinol which is isolated by filtration. The filtrate containing the soluble catalyst can be recycled directly.

The present invention is illustrated by the following examples: however, these examples should not be construed as a limitation on the scope of the present claims.

EXAMPLE 1

Addition of Trichloroacetyl Chloride to Acrylonitrile

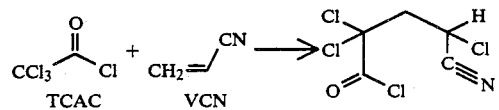

Freshly distilled trichloroacetyl chloride (TCAC), acrylonitrile (VCN) and anhydrous catalyst were heated under reflux in a nitrogen atmosphere. Percent conversion was determined by withdrawing, cooling, filtering and analyzing samples by gas chromatography (GC) or nuclear magnetic resonance (NMR) spectroscopy. Product was isolated by cooling the reaction mixture, evaporating the volatile starting materials and removing the catalyst by filtration. The results are summarized in Table I.

TABLE I

PREPARATION OF 2,2,4-TRICHLORO-4-CYANOBUTANOYL CHLORIDE FROM TRICHLOROACETYL CHLORIDE AND ACRYLONITRILE

| TCAC (moles) | VCN (moles) | Catalyst (grams) Cu° | Catalyst (grams) CuCl | Time (hrs) | % Yield Analysis | % Yield Isolated |
|---|---|---|---|---|---|---|
| 1.0 | 0.5 | — | 1.12 | 44 | 69 | — |
| 1.0 | 0.5 | — | 2.24 | 48 | >95 | — |
| 1.0 | 0.5 | — | 4.48 | 45 | 94 | — |
| 0.5 | 1.0 | — | 2.24 | 24 | — | 70 |
| 0.5 | 1.5 | — | 2.2 | 24 | — | 78 |
| 1.0 | 0.4 | — | 2.24 | 48 | — | 77 |
| 1.0 | 0.4 | 1.45 | 2.24 | 24 | — | 76 |
| 1.0 | 0.4 | 2.90 | — | 24 | 66 | 65 |
| 0.48(a) | 0.3 | 1.90 | 2.24 | 16 | 59 | 58 |
| 0.48(a) | 0.38 | 1.90 | 2.24 | 16 | 59 | 61 |
| 0.49(a) | 0.49 | 1.90 | 2.24 | 9 | 50 | 53 |
| 0.48(a) | 0.30 | 1.90 | 2.2(b) | 12 | 51 | 52 |
| 0.48 | 0.39 | 1.45 | 2.24 | 10 | 45 | 45 |
| 0.48 | 0.49 | 1.45 | 2.24 | 10 | 51 | 48 |
| 0.48 | 0.59 | 1.45 | 2.24 | 10 | 65 | 62 |
| 0.48 | 0.65 | 1.45 | 2.24 | 10 | 67 | 66 |

(a)TCAC contains an additional 15 WT % perchloroethylene
(b)recycle

EXAMPLE 2

Cyclization of 2,2,4-Trichloro-4-Cyanobutanoyl Chloride

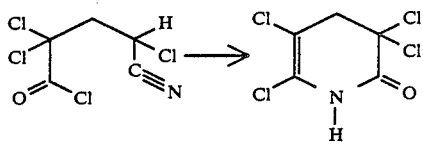

The cyclizations were carried out in a 600 milliliter (mL) Hastelloy C Bomb equipped with a magnetic drive. The 2,2,4-trichloro-4-cyanobutanoyl chloride was diluted with the desired solvent and the bomb pressurized with anhydrous HCl to the desired pressure. After stirring for the indicated time the bomb was vented and the contents transferred to a round bottom flask for evaporation on a rotary evaporator. The contents were slurried with hexane to facilitate isolation by filtration. The results are summarized in Table II.

TABLE II
CYCLIZATION OF 2,2,4-TRICHLORO-4-CYANOBUTANOYL CHLORIDE TO 3,3,5,6-TETRACHLORO-3,4-DIHYDROPYRIDIN-2-ONE

| Solvent | Temp °C. | Time (hrs) | Pressure HCl (psig) | % Yield |
|---|---|---|---|---|
| EDC[a] | 25 | 16 | 200 | 93 |
| EDC[a] | 25 | 1.5 | 100 | 92 |
| EDC[a] | 25 | 2.0 | 100 | 97 |
| EDC[a] | 25 | 2.0 | 100 | 97 |

[a]ethylene dichloride

EXAMPLE 3

Aromatization of 3,3,5,6-Tetrachloro-3,4-Dihydropyridin-2-one: Two-Phase System

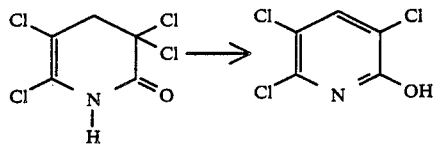

In a typical experiment 23.3 grams (g) (0.1 mol) of the dihydropyridone, 233 mL ethyl acetate, 233 mL water and 0.3 mol of base were stirred (magnetic stirrer) and refluxed for 2 hrs. After cooling, the reaction mixture was acidified with concentrated HCl and the organic phase separated and dried over MgSO4. After filtration, the product was obtained by evaporation of the solvent from the filtrate. The results are summarized in Table III.

TABLE III
AROMATIZATION OF 3,3,5,6-TETRACHLORO-3,4-DIHYDROPYRIDIN-2-ONE TO 3,5,6-TRICHLOROPYRIDIN-2-OL IN AN AQUEOUS TWO-PHASE SYSTEM

| Base | Time (hrs) | Solvents | Temp | % Yield |
|---|---|---|---|---|
| NaOH | 20+ | EDC[a]/H2O | ambient | 100 |
| Na2CO3 | 20 | EA[a]/H2O | ambient | 98 |
| Na2CO3 | 20 | EA[b]/H2O | ambient | 97 |
| Na2CO3 | 2 | EA[b]/H2O | reflux | 94 |
| Na2CO3 | 2 | EA[b]/H2O | reflux | 94 |

[a]ethylene dichloride
[b]ethyl acetate

EXAMPLE 4

Aromatization of 3,3,5,6-Tetrachloro-3,4-Dihydropyridin-2-one: Nonaqueous

To a 25 mL three neck round bottom flask was added 5 g of 3,3,5,6-tetrachloro-3,4-dihydropyridin-2-one, 0.1 g of catalyst and 25 mL of solvent. The reaction mixture was heated to reflux and reaction progress was monitored by GC. Product was recovered by filtration. In each instance isolated yields were at least 90 percent. Table IV summarizes the catalysts and solvents employed.

TABLE IV
CATALYSTS AND SOLVENTS EMPLOYED IN NONAQUEOUS AROMATIZATION OF 3,3,5,6-TETRACHLORO-3,4-DIHYDROPYRIDIN-2-ONE

| Catalyst | Solvent |
|---|---|
| 2-picoline | toluene |
| 2,6-lutidine | o-xylene |
| Tetrabutylammonium fluoride | perchloroethylene |
| Tetrabutylammonium chloride[a] | perchloroethylene |
| Tetrabutylammonium bromide | perchloroethylene |
| Tetrabutylammonium iodide | perchloroethylene |
| Tetrabutylammonium cyanide | perchloroethylene |
| Tetraphenylphosphonium chloride | perchloroethylene |
| Tetraphenylphosphonium bromide | perchloroethylene |
| Tetrabutylphosphonium acetate | perchloroethylene |
| n-Nonyltriphenylphosphonium bromide | perchloroethylene |
| MSA-1 Dow Ion Exchange Resin[b] | perchloroethylene |
| Benzyltriethylammonium chloride | perchloroethylene |
| Pyridinium chloride | perchloroethylene |
| Poly (4-vinylpyridine) | perchloroethylene |
| 18-Crown-6/KCl | perchloroethylene |

[a]recycled 5 times
[b]recycled 10 time

EXAMPLE 5

Consecutive Cyclization-Aromatization

The cyclizations were carried out in a 600 mL Hastelloy C bomb equipped with a magnetic drive. The 2,2,4-trichloro-4-cyanobutanoyl chloride (ADDUCT) was diluted with 150 mL of perchloroethylene and the bomb was pressurized to 150 psig with anhydrous HCl. After stirring for 2 hrs at the indicated temperature, the bomb was vented and the contents transferred with the aid of an additional 100 mL of perchloroethylene to a round bottom flask containing MSA-1 Dow Ion Exchange Resin. The mixture was refluxed for 1.5 hrs and the solid catalyst was removed by filtration while hot. The filtrate was cooled to crystallize the 3,5,6-trichloropyridin-2-ol which was isolated by filtration and dried. The results are summarized in Table V.

TABLE V

| Cyclization | | Aromatization | |
|---|---|---|---|
| Adduct (g) | Temp °C. | MSA Resin (g) | % Yield |
| 61 | 25° | 3.2 | 86 |
| 72 | 50° | 3.2 | 87 |
| 64 | 50° | 3.2 | 91 |

What is claimed is:

1. A process for the preparation of 2,2,4-trichloro-4-cyanobutanoyl chloride which comprises contacting trichloroacetyl chloride with acrylonitrile in the presence of a catalytic amount of copper or a cuprous salt under reflux conditions to remove HCl.

2. The process of claim 1 which is performed at atmospheric pressure or at a slight positive pressure of up to about 5 psig.

3. A process for the preparation of 3,3,5,6-tetrachloro-3,4-dihydropyridin-2-one which comprises contacting 2,2,4-trichloro-4-cyanobutanoyl chloride in an inert organic solvent with anhydrous HCl under pressure at a temperature of from ambient to about 100° C.

4. The process of claim 3 in which the inert organic solvent is selected from the group consisting of aromatic hydrocarbons, halogenated hydrocarbons and carboxylic acid esters.

5. The process of claim 3 in which the pressure is from about 5 to about 200 psig.

6. A process for the preparation of 3,5,6-trichloropyridin-2-ol which comprises treating 3,3,5,6-tetrachloro-3,4-dihydropyridin-2-one with chloride ion in an inert organic solvent.

7. The process of claim 6 in which the chloride ion is generated in situ by elimination of HCl from the dihydropyridone.

8. The process of claim 6 in which the inert organic solvent is selected from the group consisting of aromatic hydrocarbons, halogenated hydrocarbons and carboxylic acid esters.

9. The process of claim 6 in which the reaction is conducted at a temperature from about 40° to about 120° C.

10. An improved process for the preparation of 3,5,6-trichloropyridin-2-ol which comprises the following steps:
  (a) contacting trichloroacetyl chloride with acrylonitrile in the presence of a catalytic amount of copper or a cuprous salt to produce 2,2,4-trichloro-4-cyanobutanoyl chloride under reflux conditions to remove HCl;
  (b) contacting the 2,2,4-trichloro-4-cyanobutanoyl chloride in an inert organic solvent with anhydrous HCl under pressure at a temperature from ambient to about 100° C. to cyclize the butanoyl chloride to 3,3,5,6-tetrachloro-3,4-dihydropyridin-2-one; and
  (c) treating the 3,3,5,6-tetrachloro-3,4-dihydropyridin-2-one with chloride ion in an inert organic solvent to produce the 3,5,6-trichloropyridin-2-ol.

* * * * *